United States Patent [19]

Pratt

[11] 4,324,670

[45] Apr. 13, 1982

[54] PROCESS FOR MAKING A MIXED OXYALUMINUM ACYLATE COMPOSITION USEFUL IN GREASE MANUFACTURE

[75] Inventor: Charles E. Pratt, Signal Mountain, Tenn.

[73] Assignee: Chattem, Inc., Chattanooga, Tenn.

[21] Appl. No.: 201,271

[22] Filed: Nov. 4, 1980

Related U.S. Application Data

[63] Continuation-in-part of Ser. No. 96,933, Nov. 23, 1979, Pat. No. 4,280,917.

[51] Int. Cl.³ ................... C10M 5/12; C10M 7/16; C10M 1/20
[52] U.S. Cl. ................... 252/37.7; 252/35; 260/448 R; 260/448 AD
[58] Field of Search ........... 252/37.5, 37.7, 35; 260/448 R, 448 AD; 44/68

[56] References Cited

U.S. PATENT DOCUMENTS

| | | | |
|---|---|---|---|
| 2,768,138 | 10/1956 | Hotten et al. | 252/35 |
| 3,054,816 | 9/1962 | Rinse | 260/448 |
| 3,345,291 | 10/1967 | Koundakjian et al. | 252/37.7 |
| 3,591,505 | 7/1971 | Polishuk | 252/35 |
| 3,776,846 | 12/1973 | Bailey et al. | 252/37.7 |
| 3,791,972 | 2/1974 | Myers | 252/37.7 |
| 4,132,658 | 1/1979 | Coleman et al. | 252/37.7 |

FOREIGN PATENT DOCUMENTS 825878 12/1959 United Kingdom .................. 252/35

*Primary Examiner*—Thomas A. Waltz
*Attorney, Agent, or Firm*—Hill, Van Santen, Steadman, Chiara & Simpson

[57] ABSTRACT

An improved process for making a mixed oxyaluminum acylate composition wherein the mole ratio of aromatic to aliphatic radicals ranges from about to 2:3 to 19:1 and improved aluminum complex greases made using a mixed oxyaluminum acylate wherein the mole ratio of aromatic to aliphatic radicals is from about 2:3 to 3:1.

13 Claims, No Drawings

PROCESS FOR MAKING A MIXED OXYALUMINUM ACYLATE COMPOSITION USEFUL IN GREASE MANUFACTURE

RELATED APPLICATION

This application is a continuation-in-part of my earlier filed U.S. application Ser. No. 096,933 filed Nov. 23, 1979, now U.S. Pat. No. 4,280,917, the contents of which are incorporated hereinto by reference.

BACKGROUND OF THE INVENTION

The field of this invention lies in the art of making oxyaluminum acylates for use in manufacturing aluminum complex greases.

Previously I have discovered that new oxyaluminum acylates can be prepared by utilizing three carboxylic acids: An aromatic acid, an aliphatic acid, and a lower alkanoic acid. The lower alkanoic acid, during the synthetic preparation procedure, produces, as explained in my application U.S. Ser. No. 096,933, an ester by-product which is easily volatilized and removed. This process can be used to prepare oxyaluminum acylate containing not more than about 75 mole percent of aromatic carboxylic acid, and oxyaluminum acylates so produced were found to be useful in the manufacture of aluminum complex grease of apparent commercial quality.

When such three acid route is used to prepare oxyaluminum acylates containing more than about 75 mole percent of an aromatic carboxylic acid, the product oxyaluminum acylates do not appear to be useful for the manufacture of aluminum complex greases of apparent commercial quality (by using, for example, the grease preparation procedure described in my application U.S. Ser. No. 096,933).

Oxyaluminum acylate synthesized by the three acid route tend to produce product acylates which are characteristically not clear when the product acylate contains more than about 75 mole percent of an aromatic carboxylic acid. In addition, such acylates are heterogeneous in composition and are not readily soluble in organic liquids of the type conventionally used for making greases. Furthermore, greases made with such product acylates are not uniform and characteristically contain opaque solid particles. It is theorized (but there is not intent herein to be bound by theory) that the three acid route results in the production of product oxyaluminum acylates which contain lower alkanoate substituents which cause such undesirable properties for grease making purposes, particularly when one is dealing with oxyaluminum acylates containing more than about 75 mole percent of aromatic carboxylic acid.

In addition, it has now been learned that even with the oxyaluminum acylates containing up to 75 mole percent of aromatic carboxylic acid as described in my application U.S. Ser. No. 096,933, certain disadvantages exist from the standpoint of making aluminum complex greases. For one thing, during grease manufacture by the methodology described in my application U.S. Ser. No. 096,933, an acrid odor occurs, which odor suggests acetic acid vapor, are given off. These vapors are considered undesirable by grease makers.

In addition, product greases made with such oxyaluminum acylates prepared by the three acid route tend to demonstrate so-called false set characteristics (that is, the grease demonstrates an ability to become relatively rigid on standing even after a brief period of time at ambient conditions). Even though agitation of a false set grease can result in lessened viscosity, in a manner comparable to common thixotropic systems, false set is generally considered undesirable in the grease industry in a product grease for some purposes, as when the grease is to be marketed in a cartridge for cartridge-gun application (a cartridge holding viscous grease may not be applicable from the gun).

Therefore, it would be desirable to have a process for preparing oxyaluminum acylates suitable for use in making aluminum complex greases of commercial quality which does not utilize the three acid route.

BRIEF SUMMARY OF THE INVENTION

More particularly, the present invention provides an improved process for making a mixed oxyaluminum acylate composition wherein the mole ratio of aromatic to aliphatic radicals ranges from about 2:3 to 19:1 and which is adapted for use as an intermediate in the manufacture of aluminum complex greases. Also, the present invention is directed to methods for making improved aluminum complex greases using such a mixed oxyaluminum acylate composition wherein the mole ratio of aromatic to aliphatic radicals ranges from about 2:3 to 3:1 and to the greases so prepared.

Thus, the present invention in one aspect provides a process for making a composition comprised on a 100 mole percent basis of about 50 mole percent of mixed oxyaluminum acylate with the balance up to 100 mole percent thereof being mixed esters of carboxylic acid material. Not only does such a product composition appear to avoid the hereinabove described problems associated with mixed oxyaluminum acylates made by the three acid route, but also and surprisingly the product compositions appear to be readily dispersible (including solubilizable) in organic liquids of the type conventionally used in making greases. It is theorized that the presence of mixed esters of carboxylic acid material in combination with the mixed oxyaluminum acylate product for some reason not now clear promotes the dispersibility and solubilization of the mixed oxyaluminum acylate in such organic liquid.

By using such product intermediate compositions in the manufacture of aluminum complex greases, it is found that the acrid odors and the false set characteristics associated with the use of mixed oxyaluminum acylates containing up to about 75 mole percent of aromatic carboxylic acid (as made by the three acid route) are avoided.

By the present invention, then, greases can be prepared by a process step sequence wherein an aluminum alkoxide is first converted to a mixed oxyaluminum acylate in combination with mixed esters of carboxylic acid material after which such system is subject to reaction with carboxylic acids in a grease making liquid to produce a product grease.

Various other features, objects, aims, purposes, advantages, embodiments and the like, of the present invention, will be apparent to those skilled in the art from the teachings of the present invention.

DETAILED DESCRIPTION

To prepare a composition containing about 50 mole percent mixed oxyaluminum acylate, with the balance up to 100 mole percent being mixed esters of carboxylic acid material, one heats a mixture of an aluminum alkoxide material and a carboxylic acid material to a first temperature which is above the melting point of the carboxylic acid material, but which is below the boiling point of an alkanol material while agitating the mixture. Such first heating is continued for a time sufficient to form a substantially single phase liquid or a substantially uniform slurry comprised of such mixture.

In such mixture, the aluminum alkoxide material is characterized by the formula:

$$Al(OR)_3 \quad (1)$$

where R is a lower alkyl radical.

Also, in such mixture, the carboxylic acid material is comprised of:

(a) at least one aliphatic monocarboxylic acid containing from 8 to 40 carbon atoms per molecule, (b) at least one aromatic monocarboxylic acid containing from 7 to 17 carbon atoms per molecule, and (c) the mole ratio of said aromatic acid to said aliphatic acid ranging from about 2:3 to 19:1.

Also, such alkanol material is characterized by the formula:

$$ROH \quad (2)$$

where R is as defined above and where ROH is derived from reaction between said aluminum alkoxide material and said carboxylic acid material.

In such first heating, such mixture is characterized by having a mole ratio of said aluminum alkoxide material to said carboxylic acid material of about 1 to 2.

Preferably, before said first heating, said carboxylic acid material is heated to such first temperature and the aluminum alkoxide material is then admixed therewith.

After the desired single phase liquid or a substantially uniform slurry is produced by such first heating, a second heating is undertaken, preferably without any cooling. The second heating is preferably conducted with continuous agitation of the liquid, and during the second heating the liquid is heated to second temperatures in the range where such alkanol material is distilled off. The second heating is maintained or continued for a time sufficient to remove the equivalent of at least about two theoretical moles of said alkanol (per mole of aluminum alkoxide material).

Next, and preferably without cooling, the product from such second heating, a third heating is undertaken. In the third heating, the resulting product from the second heating is gradually heated to third temperatures ranging from a temperature corresponding to the final temperature of the second heating up to a temperature of about 200° C., thereby converting the resulting product from the second heating into a homogeneous liquid which has characteristically a viscosity which is substantially less than that of the product resulting from the second heating.

Preferably, the third heating is continued at such 200° C. for a time of at least about ¼ hour, and more preferably such third heating is continued at such 200° C. for a time of at least about 0.5 hour.

In one presently preferred procedure, after such third heating, the final liquid so produced is subjected to a vacuum distillation so as to remove from such final liquid any organic material therein which at atmospheric temperature and pressure boils at a temperature not more than about 250° C. Preferably, such a vacuum distillation is conducted at a pressure not above about 700 mm Hg. At such a reduced pressure, it is preferred to keep the distillation temperatures below about 200° C.

During the second heating, it is theorized that the reaction which occurs is represented by the following equation:

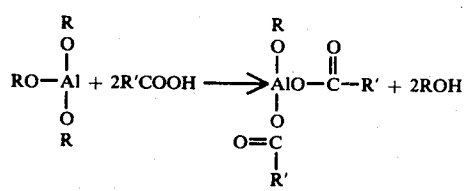

Equation I

In the above equation, R is as defined above in relation to Formulas 1 and 2 and R' is selected from the group consisting of aliphatic monocarboxylic acids and aromatic monocarboxylic acids as defined above in relation to the carboxylic acid material described.

In the third heating step, it is presently theorized that a reaction occurs which is representable by the following equations:

$$\begin{array}{c} OR \quad O \\ | \quad \| \\ Al-OCR' \xrightarrow{\Delta} O=Al-OCR' + R'-C-OR \\ | \\ O \\ | \\ O=C \\ | \\ R' \end{array}$$

Equation II and/or

Equation III $$\begin{array}{c} RO \quad O \\ \diagdown \| \\ Al-OCR' \longrightarrow \\ | \\ O \\ | \\ O=C \\ | \\ R' \end{array}$$

[cyclic aluminum carboxylate structure] + 3ROCR'

Equation III shows the reaction of preparing compounds represented by the Formula:

$$O=Al-O-C-R' \quad (3)$$
$$\quad \quad \quad \| \\ \quad \quad \quad O$$

Similarly, Equation III shows the reaction of preparing compounds represented by the Formula:

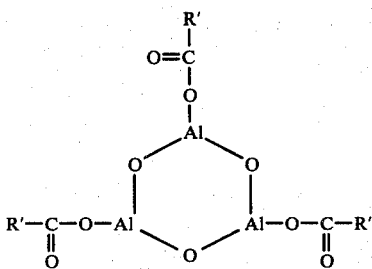

In the preceding Formulas (3) and (4), R' has its above defined meaning.

As those skilled in the art will appreciate, oxyaluminum acylates of Formulas (3) and (4), which are the mixed oxyaluminum acylates employed in the practice of the present invention, are presently believed to exist in either a monomeric form or in a cyclic trimeric form (as shown). The conditions underwhich one form exists as opposed to the other form are at this time completely unknown.

The process of the present invention through the above described third heating step is preferably carried out as a mass reaction ("neat"), but sometimes the reaction apparently can be carried out advantageously in the presence of an organic liquid phase, particularly when it is desired to use the product of such third heating step as an intermediate for grease making (as herein below described).

A presently preferred composition for use in grease manufacture comprises on a 100 weight percent total weight basis (a) from about 30 to 70 weight percent of at least one group of compounds of the Formula:

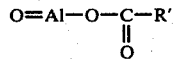

and of the Formula

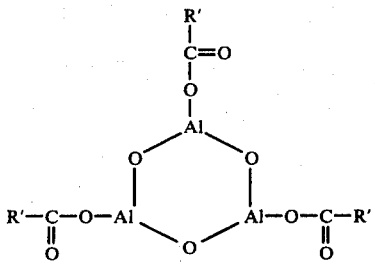

wherein R$^1$ is selected from the group of radicals consisting of:
Type (A): aliphatic radicals each containing from 10 to 38 carbon atoms, and
Type (B): aromatic radicals each containing from 6 to 16 carbon atoms, and
wherein, in any given group of such compounds, the ratio of the number of radicals of said Type (B) to said Type (A) ranges from 2:3 to 3:1, and correspondingly (b) from about 70 to 30 weight percent of a petroleum derived hydrocarbon having a viscosity at 100° F. ranging from about 35 to 50,000 SUS. Such components (a) is uniformly dispersed in such component (b) and such composition is prepared by the process above summarized and contains from about 30 to 70 weight percent of the esters above described (on a total percent weight basis).

In such a composition, such component (a) is dissolved in such component (b) preferably. Also preferably, in such component (a), such Type (A) radicals are comprised of stearyl and such Type (B) radicals are comprised of benzyl. Also preferably, in such composition, such Type (A) radicals are derived from hydrogenated tallow acids, or hydrogenated fish oils, and said Type (B) radicals are derived from benzoic acid.

A presently preferred intermediate composition from the third heating step intended for use in grease manufacture comprises on a 100 weight percent total weight basis
(a) from about 30 to 70 weight percent of at least one composition from the third heating step,
(b) from about 70 to 30 weight percent of a petroleum derived hydrocarbon having a viscosity at 100° F. ranging from about 35 to 50,000 SUS,
said component (a) being uniformly dispersed in said component (b). In such preferred grease making compositions, component (a) is dissolved in said component (b) and the total quantity of ester percent ranges from about 30 to 70 weight percent (total weight percent basis).

Aluminum trisopropoxide is presently preferred because of its availability and the relatively low boiling point of its alcohol and esters; however, other alkoxides may be used such as aluminum tri sec butoxide, and the like. The total amount of such aluminum tri alkoxide so admixed is equal to about one more aluminum alkoxide per two moles of acid.

As indicated above, such intermediate compositions can be converted into greases by the teachings of this invention without producing the undesirable acrid odor (like acetic acid), and the product greases characteristically are substantially free from unwanted false set properties when making greases using mixed oxyaluminum acylate compounds whenever the mole ratio of aromatic radicals to aliphatic radicals is less than about 3:1 in such intermediate compositions.

To make a grease of this invention using an intermediate composition as described above, one admixes such composition with a mineral starting oil having a viscosity at 100° F. of from about from about 35 to 50,000 SUS. To such product mixture, at least one carboxylic acid material as described above is added with such mixed oxyaluminum acylate with preferably both reactant types being dispersed (more preferably dissolved) in the oil. Thereafter, this mixture is heated to a temperature sufficient to produce reaction between said carboxylic acid material and said oxyaluminum acylate compound, and such contacting is continued until at least some of such oxyaluminum acylate compound has been converted into an aluminum soap. The product aluminum soap is an hydroxy aluminum diacylate. The resulting grease containing such hydroxy aluminum diacylate is then milled, if desired, and packaged. Milling can be conducted at room temperatures or at any elevated temperatures up to about 200° C. with temperatures below about 150° C. being presently preferred.

In one presently preferred grease making grease process of the present invention, the following steps are employed:

First, one heats mixtures of petroleum derived hydrocarbon oil having a viscosity at 100° F. of from about 35 to 50,000 SUS and a grease making composition as above described. This mixture contains a total amount of aluminum in the range from about 0.01 to 2.0 weight percent based on total mixture weight. Such heating is conducted at temperatures, and for times, sufficient to substantially completely disperse and preferably dissolve all starting mixed oxyaluminum acylates present in said hydrocarbon oil.

Next, one admixed with the resultant such mixture of step (A) a total of from about 0.8 to 1.2 moles (based on the total quantity of aluminum present in said resultant such mixture) of at least one carboxylic acid material selected from the group consisting of aliphatic monocarboxylic acids containing from 15 through 40 carbon atoms each and aromatic monocarboxylic acids containing from 6 through 16 carbon atoms each.

Finally, one heats and gradually raises the temperatures of the product mixture, all the while agitating such product mixture, until at least some of such starting mixed oxyaluminum acylates present in the first step have been converted into hydroxy aluminum diacylate aluminum soap by reaction in situ with said carboxylic acid material.

As indicated, in such grease making process of this invention starting mixed oxyaluminum acylates of composition of the third heating step in a base oil are reacted at least partially (preferably substantially completely) with carboxylic acid materials. A starting such mixed oxyaluminum acylate provides from a stoichiometric standpoint approximately one-half of the acylate radicals needed to produce an aluminum soap which is formed from the reaction of such mixed oxyaluminum acylate with carboxylic acid material, such aluminum soap being a compound which contains approximately two acyl groups and one hydroxyl group, each group being directly bonded to an aluminum atom (one name for such soap being hydroxyaluminum diacylate).

This hydroxyaluminum diacyl soap is made directly without the production of by-product alcohol and without water being present. The following chemical equations are illustrative of this addition reaction whereby no by-products are formed:

Equation IV where the compounds of this invention are represented by Formula (3)

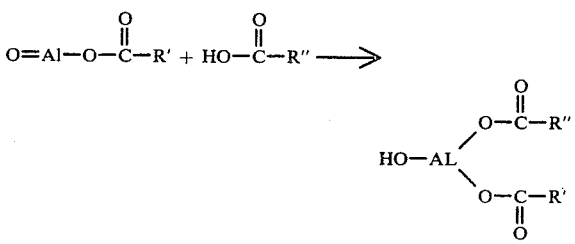

Equation V where the compounds of this invention are represented by Formula (4)

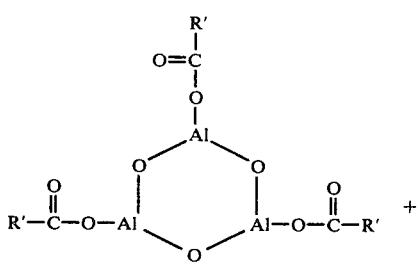

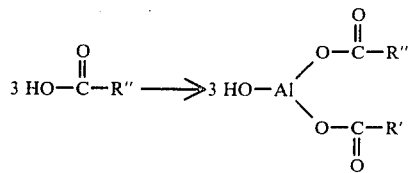

where R' is as defined above and R" is either aromatic, aliphatic or mixtures thereof, said R" radicals being supplied by the acids added by grease manufacturers practicing this process. For example, R" can preferably be the same as R' except that the ratio in any given instance, of type (B) radicals to said type (A) radicals can range from 0 to about 5:1.

In calculating the molar quantity of carboxylic acid material to be used (added) for reaction with a mixed oxyaluminum acylate in making a grease according to this invention (based on the number of carboxyl groups present in the carboxyl acid material), it is sometimes convenient to use a mole ratio ranging from about 0.8 to 1.2 of total quantity of carboxylic acid material to one mole of mixed oxyaluminum acylate.

In a grease prepared by the teachings of this invention, such an aluminum soap is preferably characterized by having the total number of acyl radicals of any given soap molecule composed of a weight ratio of aliphatic acyl groups to aromatic acyl groups ranging from about 1.3:0.7 to 0.7:1.3. Presently preferred aliphatic acyl groups are derived from fatty carboxylic acids each mixture containing an aliphatic group of at least about 16 carbon atoms. Also, presently preferred aromatic acyl groups are derived from benzoic acid.

In a grease prepared by the teachings of this invention, it is not necessary to have all of the starting mixed oxyaluminum acylate compounds converted to such an aluminum soap, although for reasons of obtaining a maximum thickening of a given base oil based upon a given quantity of mixed oxyaluminum acylate in admixture therewith, it is presently preferred to achieve a substantially complete conversion of starting mixed oxyaluminum acylate compounds into aluminum soap. However, partial conversion is sometimes preferred as when, in a given grease manufacturing situation, excess oxyaluminum acylate beyond a theoretical or calculated quantity of mixed oxyaluminum acylate is added to a starting reaction system so as to permit processing flexibility. For example, with such an excess quantity, in solution in an oil, one can add only sufficient carboxylic acid material as is necessary to achieve some predetermined system viscosity at some predetermined processing temperature, such a system viscosity having previously been determined to be characteristic of a given grease viscosity desired at ambient temperatures, according to the wishes of a given grease maker in some given instance. Such a grease could be further thickened by adding more acid later, or such a grease could be used as a "master batch" (that is, more oil and acid could subsequently be added thereto).

Although in making a grease in accordance with this invention, it is presently preferred to use, as the starting organo aluminum compound which is convertible into aluminum soap by reaction with carboxylic acid materials, only a mixed oxy aluminum acylate composition prepared by the three heating steps (because of the circumstance that no by-product alcohol is produced in converting this compound to an aluminum soap), nevertheless, as those skilled in the art will appreciate, such mixed oxyaluminum acylates may be used, if desired, in combination with other such starting organoaluminum compounds known to the prior art of grease making by forming aluminum soaps. For example, a grease maker may desire to use up stocks on hand of such prior art organoaluminum compounds gradually, or he may desire to use the compounds of this invention in combination with such prior art materials as aluminum stearate for reasons of economy or for other reasons.

In general, when such a starting organoaluminum compound mixture is used, it is preferred to employ a mixture wherein at least about 50 weight percent thereof, on a total mixture weight basis, is comprised of mixed oxyaluminum acylates present.

In its reaction with mixed oxyaluminum acylates, the hydroxyl group of a carboxyl moeity automatically goes to the aluminum of the starting mixed oxyaluminum acylates as the soap is being formed.

In addition, or in an admixture with, petroleum derived (mineral) grease making base oils, suitable specialized starting oils adapted for use in the grease making process of the present invention include lubricating oils of napthenic base, paraffinic base hydrocarbons, mixed base mineral oils, vegetable oils, synthetic oils, including synthesized hydrocarbon base fluids, alkylene polymers, polysiloxanes, ester-type oils such as dicarboxylic acid ester type oils, liquid esters of phosphorous acids, such as are shown in U.S. Pat. No. 2,768,138), and the like. In general, preferred starting base oils have viscosities at 100° F. ranging from about 35 to 50,000 SUS.

To make a grease using an oxyaluminum acylate composition of this invention in an oil, a grease maker need use no particular type of carboxylic acid material for reaction therewith. For example, it now appears that the teachings of the prior art with respect to the use of various carboxylic acids, combinations thereof, order of contacting, temperature conditions, and the like in connection with the use of the prior art aluminum alkoxides in grease making can be employed to make greases from such an oxyaluminum acylate composition, except that here no by-product alcohol is produced and no water is needed. Mono and dicarboxylic acids can be used, as can halo substituted such acids, like monochloroacetic acid, dichloroacetic acid, and the like. Examples of suitable dicarboxylic acids include succinic. One particularly preferred monocarboxylic acid is presently isostearic because such acid which is a branched $C_{18}$ saturated acid, is a relatively low viscosity liquid at ambient conditions and tends to bring down the melting point and softening point of derivatives thereof, including especially aluminum soaps thereof. For examples of U.S. patents teaching extremely wide variability in types of acids that can be added to an oil for reaction with the mixed oxyaluminum acylates of this invention to make an aluminum soap, as desired in grease making, see U.S. Pat. No. 3,476,684 (involving mono and dichloro acetic acids), U.S. Pat. No. 3,413,222 (involving succinic acid), etc. Dimer acids, such as dimerized vegetable oil carboxylic acids, such as are offered commercially by Emery Industries, can also be used as the carboxylic acid material.

A class of oxyaluminum acylate compounds to have present in a presently preferred intermediate composition prepared by the teachings of this invention comprises compounds wherein the number ratio of such Type (B) radicals to such Type (A) radicals (as defined above) ranges from about 2:3 to 3:1. In such class, the Type (B) radicals are preferably derived from benzoic acid. Such preferred compounds are relatively easy for a grease maker to convert into a grease in the presence, for example, a hydrocarbon oil. Such compounds containing a higher ratio of benzoic acids to aliphatic acids than is disclosed in the prior art, presently appear to be particularly desirable in grease making because a smaller quantity of benzoic acid is subsequently needed to complete the in situ reaction which forms the hydroxy aluminum stearate/benzoate soap. Benzoic acid itself is difficult for a grease maker to handle because of its tendency to sublime at temperatures above 100° C. Another advantage is the circumstance that, when using such a high benzoic acid derivative, one does not have to be concerned about the exact order of sequential addition of the carboxylic acid materials being reacted therewith in grease making. Both aromatic and aliphatic acids can be added simultaneously to the synthesis reaction zone. With mixed oxyaluminum acylates of the prior art which are relatively low in benzoic acid content (that is, whose content of such acid is lower than the bottom of the radical ratio just above indicated), one apparently should follow a sequential acid addition procedure (involving, for example, the addition first of long chain aliphatic fatty acid before adding benzoic acid) in order to produce a maximum thickening of oil base for a minimum total quantity of such mixed oxyaluminum acylate. Also, with such a high benzoic acid derivative, it may be that it is not necessary to have a complete reaction with mixed oxyaluminum acylate compound to produce such a maximum viscosity increase for a minimum amount of such mixed oxyaluminum acylate compound of this invention; there is presently at hand no conclusive data on this point. Further, it may be that the effect of sequential addition of carboxylic acid material is not as pronounced in this invention as it apparently is with the prior art aluminum alkoxides (see, for example, Polishuk U.S. Pat. No. 3,591,505), but, as indicated above, in the present invention, no by-product alcohol is formed during grease manufacture.

Greases made with preferred intermediate compositions prepared as taught by this invention containing mixed oxyaluminum acylates as explained can be formulated with the various additives heretofore employed in the grease making art, if desired. Thus, for example, a grease of this invention can contain one or more of such additives as rust inhibitors, anti-corrosion agents, antioxidants, dispersants, fillers, metal deactivators, pressure or anti-wear agents, tackiness agents or systems, and the like, as those skilled in the art will appreciate. Such additives may be added to a grease prior to, during, or after the aluminum soap forming step following the teachings of this invention. The quantity of additives in any given grease can, of course, vary, but a presently preferred preference is to employ less than about 15 weight percent (total grease weight basis) of such additives so as to aim toward quality product greases.

EMBODIMENTS

The present invention is further illustrated by reference to the following Examples. Those skilled in the art will appreciate that other and further embodiments are obvious and within the spirit and scope of this invention from the teachings of these present Examples taken with the accompanying specifications.

EXAMPLE 1

To a 1,000 ml. 3-neck flask the following ingredients are placed: 333.2 grams hydrogenated tallow fatty acid, 48.8 grams benzoic acid, and 67.5 grams isopropyl alcohol. This mixture is heated to approximately 80° C. at which point the contents of the flask comprises a homogeneous clear liquid system. To the flask next is added 272.3 grams of a 60% solution of aluminum isopropylate in isopropanol. This mixture is stirred and heat is applied to the flask until isopropyl alcohol begins to distill off. As the distillation continues, temperature readings are taken at 30 minute intervals and the following Table results:

TABLE I

| Pot Temperature | Vapor Temperature |
|---|---|
| 87° C. | 80° C. |
| 96° C. | 80° C. |
| 114° C. | 80° C. |
| 120° C. | 80° C. |
| 130° C. | 80° C. |
| 155° C. | 80° C. |

At this point, 92% of the theoretical isopropyl alcohol has been distilled off. More heat is then applied to the flask causing the temperature to rise to 200° C. over a period of an hour. During this time, the remainder of the alcohol on a theoretical basis is distilled off of the reaction mixture. As the temperature approaches 200°, it is observed that the mixture in the flask is a low viscosity clear amber liquid. The temperature is maintained at 200° C. for one hour. The reaction mixture is thereafter allowed to cool to room temperature. The product is a low viscosity clear amber liquid. The aluminum is analyzed to be 4.80% and by analysis the oxyluminum acylate is found to have 42.7% benzoic radicals. The oxyaluminum acylate is dissolved in a mixture of isopropyl benzoate and isopropyl hydrogenated tallowate.

EXAMPLE 2

Grease for Example 1

To 301.4 grams of a grease base oil having the viscosity at 100° F. of 1766 SUS is added 36.4 grams of the compound from Example 1. The resulting mixture is stirred and gradually heated to 90° C. where it is observed that a clear solution results. At this point there is added to the heated system simultaneously 8.7 grams hydrogenated tallow fatty acid and 3.4 grams benzoic acid with stirring. The amount of ingredients added to the base oil in this grease making Example is calculated in such a manner as to produce a final grease with an aluminum content of 0.5% aluminum metal, a fatty to benzoic ratio of 1.1 to 0.9 and a ratio of 1.92 moles total acids per atom of aluminum. Heating is continued and the temperature is gradually raised to a temperature of 200° C. and the mixture is held at 200° C. for one-half hour. After the acids are added, and as the temperature is thus gradually increased, gradual thickening of the system is observed. The reaction mixture remains clear throughout the heating process and results in a clear grease. No acetic acid odor is detected during this process. After the reaction mixture is held for one-half hour at 200° C., it is allowed to cool and physical properties are determined. The resultant clear grease has a dropping point of 495° F. and an unworked penetration of 311. After working 60 strokes in a standard grease worker, the penetration is 288. The grease remains soft and pliable after standing overnight indicating the absence of false set properties.

EXAMPLE 3

To a 22 liter 3-neck flask is added the following ingredients: 4,998.6 grams hydrogenated tallow fatty acid, 2,197.8 grams benzoic acid and 3,816 grams isopropanol. This mixture is heated to approximately 60° C. at which point the mixture is a clear low viscosity homogenous liquid. To this mixture is then added 3,675.6 grams granulated aluminum isopropylate. Heat is applied to the flask and the temperature gradually raised to the point where isopropanol begins to distill off. As the distillation continues temperature readings are taken at 60 minute intervals and the following Table results:

TABLE II

| Pot Temperature | Vapor Temperature |
|---|---|
| 84° C. | 81° C. |
| 85° C. | 81° C. |
| 85° C. | 81° C. |
| 85° C. | 81° C. |
| 93° C. | 81° C. |
| 100° C. | 81° C. |
| 120° C. | 81° C. |
| 166° C. | 84° C. |

At this point, the heating causes the temperature to begin rising much more rapidly and it reaches 200° C. within another hour.

During the time of the first and second steps of heating, both the added isopropyl alcohol and 2 moles of produced isopropyl alcohol on a theoretical basis are removed from the flask. The temperature is then maintained at 200° C. for one more hour after which it is allowed to cool. The product is a light amber clear liquid which is analyzed to be 5.67% aluminum and by further analysis it is determined that the oxyaluminum acylate so produced contained 75.3% benzoic radicals. The oxyaluminum acylate is dissolved in a mixture of isopropyl benzoate and isopropyl hydrogenated tallowate.

EXAMPLE 4

Grease from Example 3

To 303.8 grams of a grease base oil having the viscosity at 100° F. of 1766 SUS is added 30.8 grams of the compound from Example 3. The resulting mixture is stirred and gradually heated to 90° C. where it is observed that a clear solution results. At this point there is added to the heated system simultaneously 14.3 grams hydrogenated tallow fatty acid and 0.9 grams benzoic acid with stirring. The amount of ingredients added to the base oil in this grease making Example is calculated in such a manner as to produce a final grease with an aluminum content of 0.5% aluminum metal, a fatty to benzoic ratio of 1.1 to 0.9 and a ratio of 1.92 mole total acids per atom of aluminum. Heating is continued and the temperature is gradually raised to a temperature of 200° C. and the mixture is held at 200° C. for one-half hour. After the acids are added, and as the temperature is thus gradually increased, gradual thickening of the system is observed. The reaction mixture remains clear throughout the heating process and results in a clear grease. No acetic acid odor is detected during this process. After the reaction mixture is held for one-half hour at 200° C., it is allowed to cool and physical properties are determined. The resultant clear grease has a dropping point of 509° F. and an unworked penetration of 245. After working 60 strokes in a standard grease worker, the penetration is 286. The grease remains soft and pliable after standing overnight indicating the absence of false set properties.

To a 3 liter resin kettle equipped with a stirring motor and a lid with 3 openings is added the following ingredients: 687.3 grams hydrogenated tallow fatty acids, 503.7 grams benzoic acid, and 673.9 grams isopropyl alcohol. This mixture is heated until it becomes a homogenous clear solution at approximately 60° C. To this mixture while stirring is then added 673.9 grams powdered aluminum isopropylate. Heat is then applied to the reaction vessel until it rises to a temperature where isopropyl alcohol begins to distill off. The distillation is continued and periodic temperature readings are taken and the following Table results:

TABLE III

| Hours | Pot Temperature | Vapor Temperature |
|---|---|---|
| 0 | 85° C. | 81° C. |
| 1½ hrs. | 85° C. | 81° C. |
| 2 hours | 85° C. | 80° C. |
| 3¾ hrs. | 205° C. | 65° C. |

During the above distillation procedure, both the added isopropyl alcohol and the 2 moles isopropyl alcohol per atom aluminum produced by the reaction process are removed from the reaction vessel on a theoretical basis. Heating is continued at 200° C. for 1 ½ hours and then the reaction mixture is allowed to cool. The product is a light amber clear oily liquid. The aluminum is analyzed to be 5.86% and by further analysis it is determined that the oxyaluminum acylate contains 85% benzoic radicals. The oxyaluminum acylate is dissolved in a mixture of isopropyl benzoate and isopropyl hydrogenated tallowate.

EXAMPLE 6

Grease From Example 5

To 303.7 grams of a grease base oil having 9 viscosity at 100° F. at 1766 SUS is added 29.8 grams of the compound from Example 5. The resulting mixture is stirred and gradually heated to 90° C. where is is observed that a homogenous relatively clear mixture results. At this point there is added to the heated system simultaneously 16.3 grams hydrogenated tallow fatty acid and 0.1 grams benzoic acid with stirring. The amount of ingredients added to the base oil in this grease making Example is calculated in such a manner as to produce a final grease with an aluminum content of 0.5% aluminum metal, a fatty to benzoic ratio of 1.1 to 0.9 and a ratio of 1.92 moles total acids per atom of aluminum. Heating is continued and the temperature is gradually raised to a temperature of 200° C. and mixture is held at 200° C. for one-half hour. After the acids are added, and as the temperature is thus gradually increased, gradual thickening of the system is observed. The reaction mixture remains clear throughout the heating process and results in a clear grease. No acetic acid odor is detected during this process. After the reaction mixture is held for one-half hour at 200° C., it is allowed to cool and physical properties are determined. The resultant clear grease has a dropping point of 468° F. and an unworked penetration of 307. After working 60 strokes in a standard grease worker, the penetration is 314. The grease remains soft and pliable after standing overnight indicating the absence of false set properties.

EXAMPLE 7

Attempt to Make 85 Mole % Benzoic Mixed Oxyaluminum Acylate Via the Acetic Acid Process To a 1000 ml. 3-neck flask is added the following ingredients: 183.2 grams Coray 22 which is a lubricating base oil having an approximate viscosity of 100 SUS at 100° F., 50 grams isopropyl alcohol, 48 grams glacial acetic acid, 33.3 grams hydrogenated tallow fatty acids, and 83.0 grams benzoic acid. The temperature of this mixture is raised to 55° C. at which point 163.4 grams powdered aluminum isopropylate is added to the flask. This mixture is stirred and gradually increased to a point where isopropanol begins to distill off. As the distillation continues, periodic temperature readings are taken and the following Table results:

TABLE IV

| Hours | Pot Temperature | Vapor Temperature |
|---|---|---|
| 0 | 89° C. | 81° C. |
| 0.5 | 96° C. | 81° C. |
| 1.0 | 156° C. | 80° C. |
| 1.25 | 198° C. | 81° C. |
| 1.5 | 202° C. | 65° C. |
| 2.0 | 210° C. | 30° C. |
| 2.5 | 194° C. | 30° C. |
| 4.0 | 192° C. | 30° C. |

During this distillation procedure, the material in the flask never goes through a clear stage and does not end up clear. It is only thin when the temperature rises to approximately 200° C.; however, it is still an opaque liquid at this point. Very little distillate is taken off between the temperatures of 156° C. and 200° C. indicating that only a small amount of isopropyl acetate ester is formed by this reaction. The total distillate measures 149 grams and accounts for little more than the theoretical isopropanol released by the acids plus the 50 grams sopropyl alcohol added to facilitate dispersion of the initial materials.

EXAMPLE 8

The experiment in Example 7 is repeated to make sure that the results are reliable. The quantities of ingredients are added in the same order and the mixture is stirred and the temperature gradually increased to a point where isopropanol begins to distill off. As the distillation continues temperature readings are taken and the following Table results:

TABLE V

| Hours | Pot Temperature | Vapor Temperature |
|---|---|---|
| 0 | 90° C. | 81° C. |
| .5 | 93° C. | 81° C. |
| 1.0 | 180° C. | 81° C. |
| 1.5 | 200° C. | 35° C. |
| 2.0 | 180° C. | 23° C. |
| 2.5 | 202° C. | 23° C. |
| 3.5 | 196° C. | 23° C. |
| 4.0 | 194° C. | 23° C. |
| 4.5 | 197° C. | 23° C. |
| 5.0 | 197° C. | 23° C. |
| 5.5 | 203° C. | 23° C. |
| 6.0 | 200° C. | 23° C. |

During this experiment extra care is taken to ensure that excessive heat does not damage or interfere with the reaction. At no time does the temperature ever exceed 205° C. As can be seen by the Table, no appreciable isopropyl acetate is taken off as indicated by the low vapor temperatures which are recorded as the pot temperature moves towards 200° C. As with Example 7, the mixture in the flask never turns clear and remains an opaque heterogenous mixture.

EXAMPLE 9

An attempt is made to make a grease from the material produced in Example 8. 302.2 grams of the same grease base oil as employed in Example 6 are placed in a beaker which contains a magnetic stir bar. This beaker is placed on a hot plate and heated with stirring to a temperature of 160° C. 31.4 grams of the product obtained from Example 8 is melted and added to the oil. During this addition, it is noted that solid particles start forming immediately. The size of the particles are about 1/16th of an inch to ⅛th of an inch in diameter. The mixture is then heated to 200° C. in an attempt to disperse the particles, but this is not successful. The temperature is then lowered to 95° C. at which temperature 16.3 grams hydrogenated tallow fatty acid are added slowly to the mixture under agitation. Then 0.1 gram benzoic acid is added immediately following this addition of the hydrogenated tallow fatty acids and it is noted that the temperature is 100° C. when the benzoic acid is in. The particles noted above do not disappear. The mixture is then raised again to a temperature of 200° C. The mixture thickens slightly, but still contains the solid opaque particles. Because of the solid opaque particles, this material does not appear to be a usable grease.

EXAMPLE 10

Preparation of Mixed Oxyaluminum Acylate Containing 75 mole % Benzoic Acid Via the Acetic Acid Method To a 1000 ml. 3-neck flask is added 198.4 grams Coray 22 oil (lubricating base oil having an approximate viscosity of 100 SUS at 100° F.). To this oil in such a flask is added the following ingredients: 50 grams isopropyl alcohol, 48 grams acetic acid, 55.5 grams hydrogenated tallow fatty acids, 73.3 grams benzoic acid. This mixture is warmed slightly to produce a homogenous clear liquid. The temperature is then raised to 65° C. and at this point is added to the system 163.4 grams aluminum isopropylate.

This mixture is stirred and the temperature gradually increased to a point where isopropanol begins to distill off. As the distillation continues periodic temperature readings are taken and the following Table results:

TABLE VI

| Hours | Pot Temperature | Vapor Temperature |
|-------|-----------------|-------------------|
| 0     | 88° C.          | 81° C.            |
| .5    | 88° C.          | 81° C.            |
| 1.0   | 90° C.          | 81° C.            |
| 1.5   | 99° C.          | 81° C.            |
| 2.0   | 110° C.         | 81° C.            |
| 2.5   | 180° C.         | 84° C.            |
| 3.0   | 200° C.         | 87° C.            |
| 3.5   | 200° C.         | 87° C.            |
| 4.0   | 204° C.         | 87° C.            |

During the distillation a total of 2 moles isopropyl alcohol are removed after which 1 mole of isopropyl acetate is removed all on a theoretical basis. The reaction mixture is thereafter allowed to cool to room temperature. The product is a clear solid amber material having a melting point of approximately 130° C. and by calculation is found to contain 5.44% aluminum indicating a 40.9% solution (in 100 SUS 100° F. lubricating oil) of mixed oxyaluminum stearate/benzoate wherein the mole percent benzoate is 75%.

EXAMPLE 11

Grease Made From Example 10

303.5 grams of the same grease base oil as employed in Example 6 are placed in a beaker which contains a magnetic stir bar. This beaker is placed on a hot plate and is heated with stirring to a temperature of 160° C. 32.2 grams of the product obtained from Example 10 is melted and added to the oil. Heating is continued with stirring and the temperature is gradually raised to a temperature of 200° C. and it is observed that the mixture is uniformly dispersed. The temperature is then lowered to 95° C. at which temperature 14.5 grams hydrogenated tallow fatty acid are added slowly to the mixture under agitation. Then, 0.9 grams benzoic acid are added immediately following this addition of the hydrogenated tallow fatty acids. The amount of ingredients added to the base oil in this grease making Example is calculated in such a manner as to produce a final grease with an aluminum content of 0.5% aluminum metal, a fatty to benzoic ratio of 1.1 to 0.9 and a ratio of 1.92 moles total acids per atom of aluminum. The mixture is again raised to a temperature of 200° C. and during such a period of heating is observed an acrid odor resembling acetic acid.

After the acids are added, and as the temperature is thus gradually increased, gradual thickening of the system is observed. The reaction mixture remains clear throughout the heating process and results in a clear grease. After the reaction mixture is held for 15 minutes at 200° C., it is allowed to cool and physical properties are determined. The resultant clear grease has a dropping point of 479° F. and an unworked penetration of 301. After working 60 strokes in a standard grease worker, the penetration is 314.

As those skilled in the art will appreciate, minor amounts of various carboxylic acids known to the art of grease making can be present, if desired, in the reactants employed to make a grease as described herein.

I claim:

1. A process for making a composition comprised of mixed oxyaluminum acylate and mixed esters of carboxylic acid material, said process comprising the steps of sequentially,
   (A) first heating a mixture of an aluminum alkoxide material and a carboxylic acid material to a first temperature which is above the melting point of said carboxylic acid material but which is below the boiling point of an alkanol material while agitating said mixture, said first heating being continued for a time sufficient to form a substantially homogeneous mixture,
     (1) said aluminum alkoxide material being characterized by the formula:

$Al(OR)_3$ where R is a lower alkyl radical,
     (2) said carboxylic acid material being comprised of:
       (a) at least one aliphatic monocarboxylic acid containing from 8 to 40 carbon atoms per molecule, and (b) at least one aromatic monocarboxylic acid containing from 7 to 14 carbon atoms per molecule, (c) the mole ratio of said aromatic acid to said aliphatic acid ranging from about 2:3 to 19:1.

(3) said alkanol material being characterized by the formula:

ROH where R is defined above and where ROH is derived from reaction between said aluminum alkoxide material and said carboxylic acid material, (4) the mole ratio of said aluminum alkoxide material to said carboxylic acid material is about 1 to 2, (B) secondly heating said liquid to second temperatures in the range where said alkanol material is distilled off and maintaining said second heating for a time sufficient to remove the equivalent of at least about 2 theoretical moles of said alkanol based upon said aluminum alkoxide material, and (C) thirdly heating the resulting product from said second heating to gradually increasing third temperatures from a temperature corresponding to the final temperature of said second heating up to about 200° C., thereby to convert said resulting product into a homogeneous final liquid having a viscosity substantially less than that of said resulting product from said second heating.

2. The process of claim 1 wherein said third heating is continued at said 200° C. for a time of at least about ¼ hour.

3. The process of claim 1 wherein said third heating is continued at said 200° C. for a time of at least about 0.5 hour.

4. The process of claim 1 wherein, before said first heating, said carboxylic acid material is heated to said first temperature and said aluminum alkoxide material is then admixed therewith.

5. The process of claim 1 wherein up to about 50 weight percent of added alkanol material is admixed with said mixture in said first heating.

6. The process of claim 1 wherein after said third heating said final liquid is subjected to vacuum distillation so as to remove from said final liquid any organic material therein which at atmospheric temperature and pressure boils at a temperature not more than about 250° C.

7. The process of claim 6 wherein said vacuum distillation is conducted at a pressure not above about 700 mm Hg.

8. A composition for use in grease manufacture comprising on a 100 weight percent total weight basis, (A) from about 30 to 70 weight percent of at least one group of compounds of the formula:

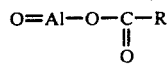

and of the formula:

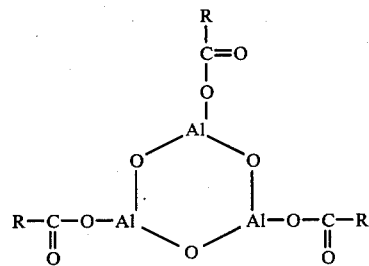

wherein R is selected from the group of radicals consisting of:

Type (A): aliphatic radicals each containing from 8 to 40 carbon atoms, and

Type (B): aromatic radicals each containing from 7 to 14 carbon atoms, and wherein, in any given such compound, the ratio of the number or radicals of said type (B) to said Type (A) ranges from 2:3 to 3:1, said compounds having been prepared by the process of claim 1, and correspondingly (B) from about 30 to about 70 weight percent of a petroleum derived hydrocarbon having a viscosity at 100° F. ranging from about 35 to 50,000 SUS, said component (A) being uniformly dispersed in said component (B).

9. The composition of claim 8 wherein said component (A) is dissolved in said component (B).

10. The composition of claim 8 wherein in said component (a), said Type (A) radicals are comprised of stearyl and said type (B) radicals are comprised of benzyl.

11. The composition of claim 8 wherein said Type (A) radicals are derived from hydrogenated tallow acids, and said Type (B) radicals are derived from benzoic acid.

12. A process for making a grease comprising the steps of (A) heating a mixture of petroleum derived hydrocarbon having a viscosity at 100° F. of from about 35 to 50,000 SUS and a composition of claim 8, said mixture containing a total amount of aluminum in the range from about 0.01 to 2.0 weight percent based on total mixture weight, said heating being conducted at temperatures, and for times, sufficient to substantially completely dissolve all starting mixed oxyaluminum acylates present in said hydrocarbon, (B) admixing with the resultant such mixture of step (A) a total of from about 0.8 to 1.2 moles per mole of said oxyaluminum acylate present in said resultant such mixture of at least one carboxylic acid material selected from the group consisting of aliphatic monocarboxylic acids containing from 10 through 40 carbon atoms each and aromatic monocarboxylic acids containing from 7 through 28 carbon atoms each, and (C) thereafter heating and gradually raising the temperature of the product mixture until at least some of said starting mixed oxyaluminum acylates present in step (A) have been converted into diacyl monohydroxy aluminum soap by reaction in situ with said carboxylic acid material.

13. A grease prepared by the process of claim 12.

* * * * *